United States Patent
Kimbrel et al.

(10) Patent No.: US 8,822,218 B2
(45) Date of Patent: Sep. 2, 2014

(54) METHOD OF GENERATING NATURAL KILLER CELLS AND DENDRITIC CELLS FROM HUMAN EMBRYONIC STEM CELL-DERIVED HEMANGIOBLASTS

(75) Inventors: Erin Kimbrel, Marlborough, MA (US); Shi-Jiang Lu, Shrewsbury, MA (US)

(73) Assignee: Stem Cell & Regenerative Medicine International, Inc., Los Angeles, CA (US)

( * ) Notice: Subject to any disclaimer, the term of this patent is extended or adjusted under 35 U.S.C. 154(b) by 0 days.

(21) Appl. No.: 13/512,795

(22) PCT Filed: Dec. 1, 2010

(86) PCT No.: PCT/US2010/058593
§ 371 (c)(1),
(2), (4) Date: Jul. 18, 2012

(87) PCT Pub. No.: WO2011/068896
PCT Pub. Date: Jun. 9, 2011

(65) Prior Publication Data
US 2012/0282693 A1    Nov. 8, 2012

Related U.S. Application Data

(60) Provisional application No. 61/266,661, filed on Dec. 4, 2009.

(51) Int. Cl.
*C12N 5/00* (2006.01)
*C12N 5/02* (2006.01)

(52) U.S. Cl.
USPC .......................................... 435/377; 435/325

(58) Field of Classification Search
None
See application file for complete search history.

(56) References Cited

U.S. PATENT DOCUMENTS

| 2004/0013676 A1* | 1/2004 | Bae et al. .................. 424/184.1 |
| 2011/0064705 A1 | 3/2011 | Lanza et al. |
| 2011/0086424 A1 | 4/2011 | Lanza et al. |

FOREIGN PATENT DOCUMENTS

| CN | 102822332 A | 12/2012 |
| EP | 2507365 | 10/2012 |
| JP | 2013512673 | 4/2013 |
| WO | 2007120811 A2 | 10/2007 |
| WO | 2009137624 A2 | 11/2009 |
| WO | 2009137629 A2 | 11/2009 |
| WO | 2011068896 A1 | 6/2011 |

* cited by examiner

*Primary Examiner* — Karen Cochrane Carlson
*Assistant Examiner* — Natalie Moss
(74) *Attorney, Agent, or Firm* — Seth D. Levy; Nixon Peabody, LLP (57) ABSTRACT

This invention provides methods of generating natural killer (NK) cells and dendritic cells (DCs). The methods utilize human hemangioblasts as intermediate cells to generate the NK cells and DCs. In various embodiments, the methods do not require the use of stromal feeder layers.

12 Claims, 9 Drawing Sheets

METHOD OF GENERATING NATURAL KILLER CELLS AND DENDRITIC CELLS FROM HUMAN EMBRYONIC STEM CELL-DERIVED HEMANGIOBLASTS

CROSS-REFERENCE TO RELATED APPLICATIONS

This application is a National Phase of International Application No. PCT/US10/58593, filed Dec. 1, 2010, which designated the U.S. and that International Application was published under PCT Article 21(2) in English. This application also includes a claim of priority under 35 U.S.C. §119(e) to U.S. provisional patent application No. 61/266,661, filed Dec. 4, 2009.

FIELD OF INVENTION

This invention relates to the generation of natural killer (NK) cells and dendritic cells (DCs) from hemangioblasts.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Studies with human and mouse embryonic stem cells (ESCs) have shown that a common precursor to both vascular (endothelial and smooth muscle cells) and hematopoietic cell lineages called the hemangioblast can be produced from ESC-derived embryoid bodies in culture. The inventors' group has developed a simple strategy to efficiently and reproducibly generate hemangioblasts from multiple hESC lines under serum- and stromal-free conditions, which is important for their productive use in regenerative medicine. Previous work his shown that hESC-derived hemangioblasts can effectively differentiate into erythroid and myeloid lineages, but their ability to produce lymphoid lineage cells, including those with immunotherapeutic potential, is relatively unknown.

Natural killer (NK) cells, which arise through the lymphoid lineage and are part of the innate immune system, may be used in anti-cancer therapy as they have been found to detect and kill certain types of tumor cells. Dendritic cells (DCs), which mostly arise through the myeloid lineage (from monocytes) and are part of the adaptive immune system, may be used to enhance antigen-specific immune responses through their ability to present antigen to and stimulate both naïve and memory T cells (e.g., DC-based vaccine therapy).

Given the immunotherapeutic potential, there exists a need in the art for a method of generating natural killer (NK) cells and dendritic cells (DCs).

SUMMARY OF THE INVENTION

The following embodiments and aspects thereof are described and illustrated in conjunction with compositions and methods which are meant to be exemplary and illustrative, not limiting in scope.

Various embodiments of the present invention provide for a method Of generating natural killer (NK) cells comprising: providing hemangioblasts; culturing the hemangioblasts on methylcellulose and a first cytokine mixture comprising IL2, IL3, IL6, IL7, IL15, SCF and FL; harvesting the cultured cells; and culturing the harvested cells in liquid media comprising human serum, and a second cytokine mixture comprising IL7, IL15, SCF and FL to generate NK cells.

In various embodiments, the methylcellulose can be H4236 methylcellulose. In other embodiments, the methylcellulose can be H4536 methylcellulose.

In various embodiments, the concentration of IL2 can be about 5-10 ng/ml, IL3 can be about 1-10 ng/ml, IL6 can be about 1-10 ng/ml, IL7 can be about 5-20 ng/ml, IL15 can be about 5-10 ng/ml, SCF can be about 10-50 ng/ml, and FL can be about 10-50 ng/mL In various embodiments, culturing the hemangioblasts can be for about 6 to 8 days. In various embodiments, culturing the harvested cells can be for about 14 to 21 days. In various embodiments, the method can further comprise weekly media changes to refresh the second cytokine mixture.

In various embodiments, the hemangioblasts can be differentiated from human embryonic stem cells (hESCs). In other embodiments, the hemangioblasts can be differentiated from induced pluripotent (iPS) cells.

In various embodiments, the NK cells can be immature NK cells and can be CD56+ and CD16−. In other embodiments, the NK cells can be mature NK cells and can be CD56− and CD 16+, or CD56lo and CD16+.

Various embodiments of the present invention provide for a method of generating natural killer (NK) cells comprising: providing hemangioblasts; culturing the hemangioblasts in liquid media comprising human serum and a first cytokine mixture comprising IL2, IL3, IL6, IL7, IL15, and SCF; harvesting the cultured cells; and culturing the harvested cells in liquid media comprising human serum and a second cytokine mixture comprising IL7, IL15, SCF and FL to generate the NKs.

In various embodiments, the concentration of IL2 can be about 5-10 ng/ml, IL3 can be about 1-10 ng/ml, IL6 can be about 1-10 ng/ml, IL7 can be about 5-20 ng/ml, IL15 can be about 5-10 ng/ml, SCF can be about 10-50 ng/ml, and FL can be about 10-50ng,/ml.

In various embodiments, culturing the hemangioblasts can be for about 6 to 8 days. In various embodiments, culturing the harvested cells can be for about 14 to 21 days.

In various embodiments, the method can further comprise weekly media changes to refresh the second cytokine mixture.

In various embodiments, the hemangioblasts can be differentiated from human embryonic stem cells (hESCs). In other embodiments, the hemangioblasts can be differentiated from induced pluripotent (iPS) cells.

In various embodiments, the NK cells can be immature NK cells and can be CD56+ and CD 16−. In other embodiments, the NK cells can be mature NK cells and can be CD56− and CD 16+, or CD56lo and CD 16+.

Various embodiments of the present invention provide for a natural killer (NK) cell generated by any of the methods of the present invention. Other embodiments of the present invention provide for a pharmaceutically acceptable composition comprising a quantity of the NK cells generated by any of the method of the present invention.

Various embodiments of the present invention provide for a method to generate dendritic cells (DCs), comprising: providing hemangioblasts; culturing the hemangioblasts in liquid media comprising human serum, SCF, FL, IL3 and GM- CSF; adding IL4 to the liquid media; and further culturing the hemangioblasts to generate the DCs.

In various embodiments, culturing the hemangioblasts can be for about 7 to 11 days. In various embodiments, the culturing of the hemangioblast after the addition of IL4 can be for about 8 to 10 days.

In various embodiments, the method can further comprise adding a cytokine mixture comprising IL1b, TNFα and IL6 to induce maturation of the DCs. In various embodiments, the cytokine mixture can be added for about 48 hours. In various embodiments, the cytokine mixture can further comprise a cytokine selected from the group consisting of PGE2, IFNα2b, poly I:C, IFNγ and combinations thereof.

In various embodiments, the method can further comprise adding LPS, IFNγ and/or S-28463 to stimulate IL12p70 production from the DCs and/or HLA-DR expression from the DCs.

In various embodiments, the concentration of SCF can be about 20-100 ng/ml, FL can be about 10-50 ng/ml, IL3 can be about 5-50 ng/ml, GM-CSF can be about 50-100 ng/ml, and IL4 can be about 50-100 ng/ml. In various embodiments, the concentration of IL1b can be about 10 ng/ml, TNFγ can be about 10 ng/ml, and IL6 can be about 150 ng/ml. In various embodiments, the concentration of PGE2 can be about 1 µg/ml, IFNα2b can be about 3000 units/ml, poly I:C can be about 20 µg/ml, and IFNγ can be about 20 ng/ml.

In various embodiments, the DCs can be mature DCs and express CD83. In other embodiments, the DCs can be mature DCs and the expression of CD209, HLA DR and/or CD11c is increased.

Various embodiments of the present invention provide for a dendritic cell (DC) generated by any of the methods of the present invention. Other embodiments of the present invention provide for a pharmaceutically acceptable composition comprising a quantity of the DCs generated by any of the method of the present invention.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
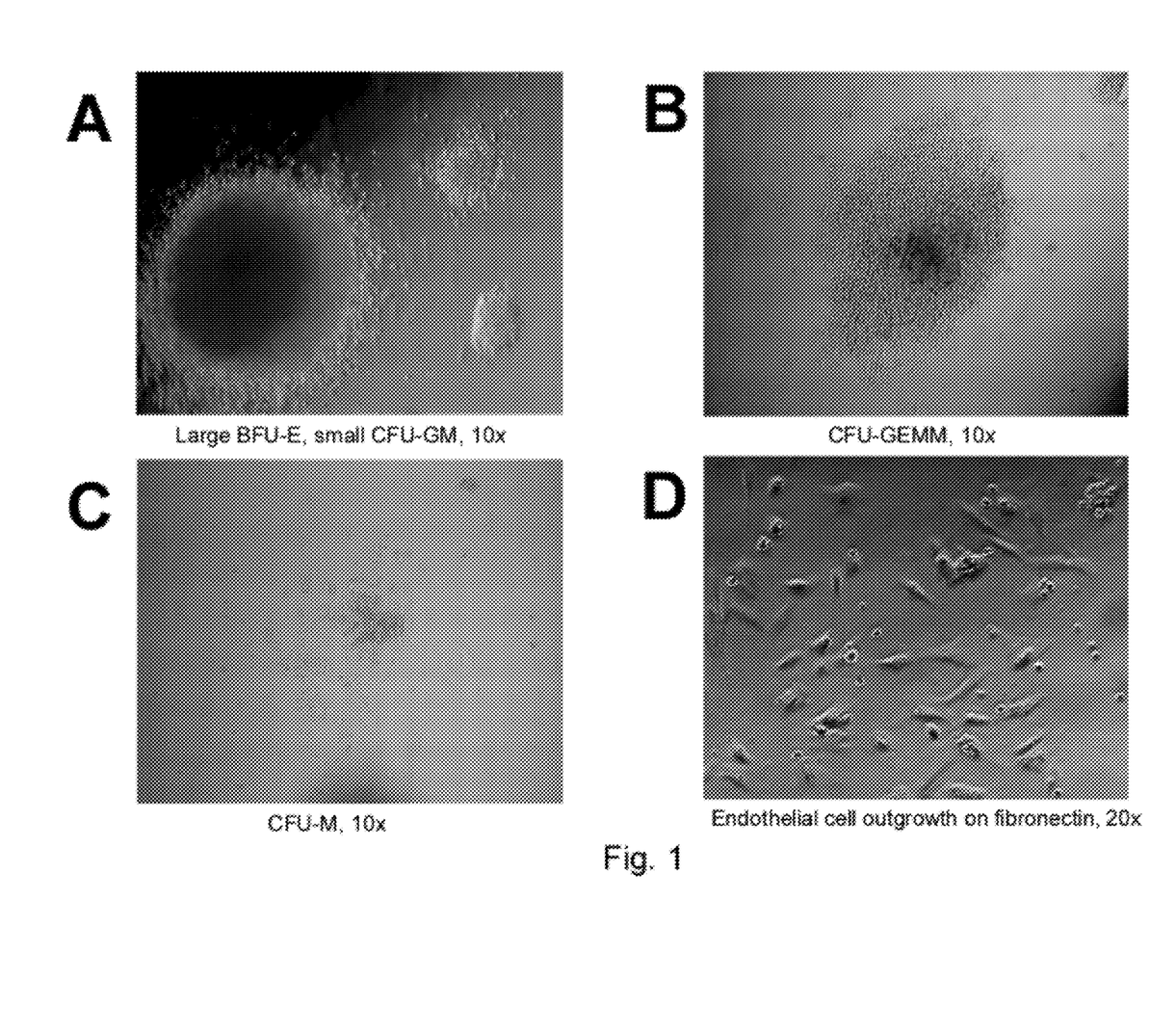
FIG. 1 shows that hemangioblasts are bipotential precursor cells that can give rise to both hematopoietic (A-C) and vascular (D-F) lineages in accordance with various embodiments of the present invention.
Figure 2:
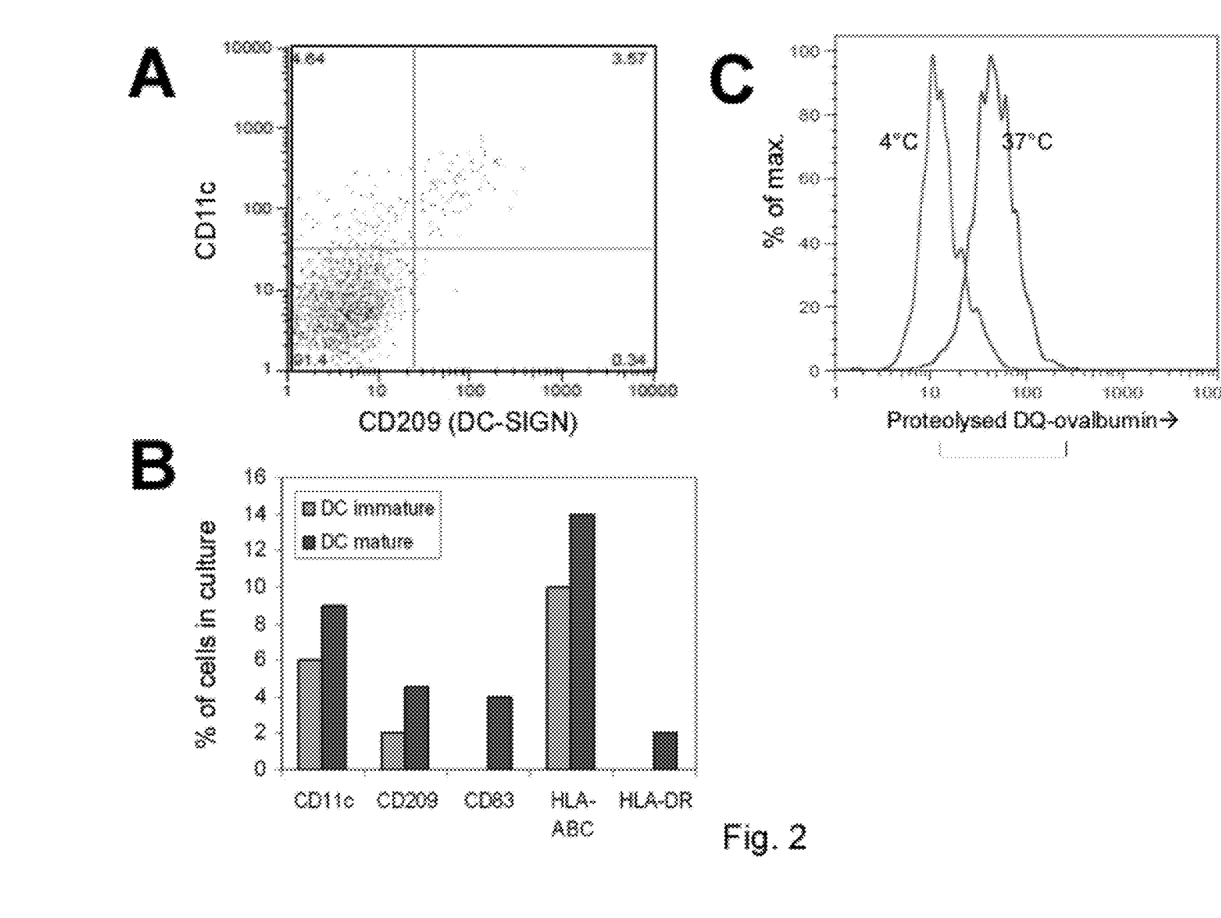
FIG. 2 shows that cells with immunotherapeutic potential, such as dendritic cells can be differentiated from hemangioblasts in accordance with various embodiments of the present invention. A. Dendritic cell surface marker expression at day 28 of differentiation. B. Bar graph showing 48 hours exposure to maturation cytokines can increase DC surface marker expression. C. Histogram showing DCs can take up and process DQ-ovalbumin antigen in a 30 minute assay. D. Wright-Giemsa stain of DCs, 20×. E. Wright-Giemsa stain of DCs, 100×.
Figure 3:
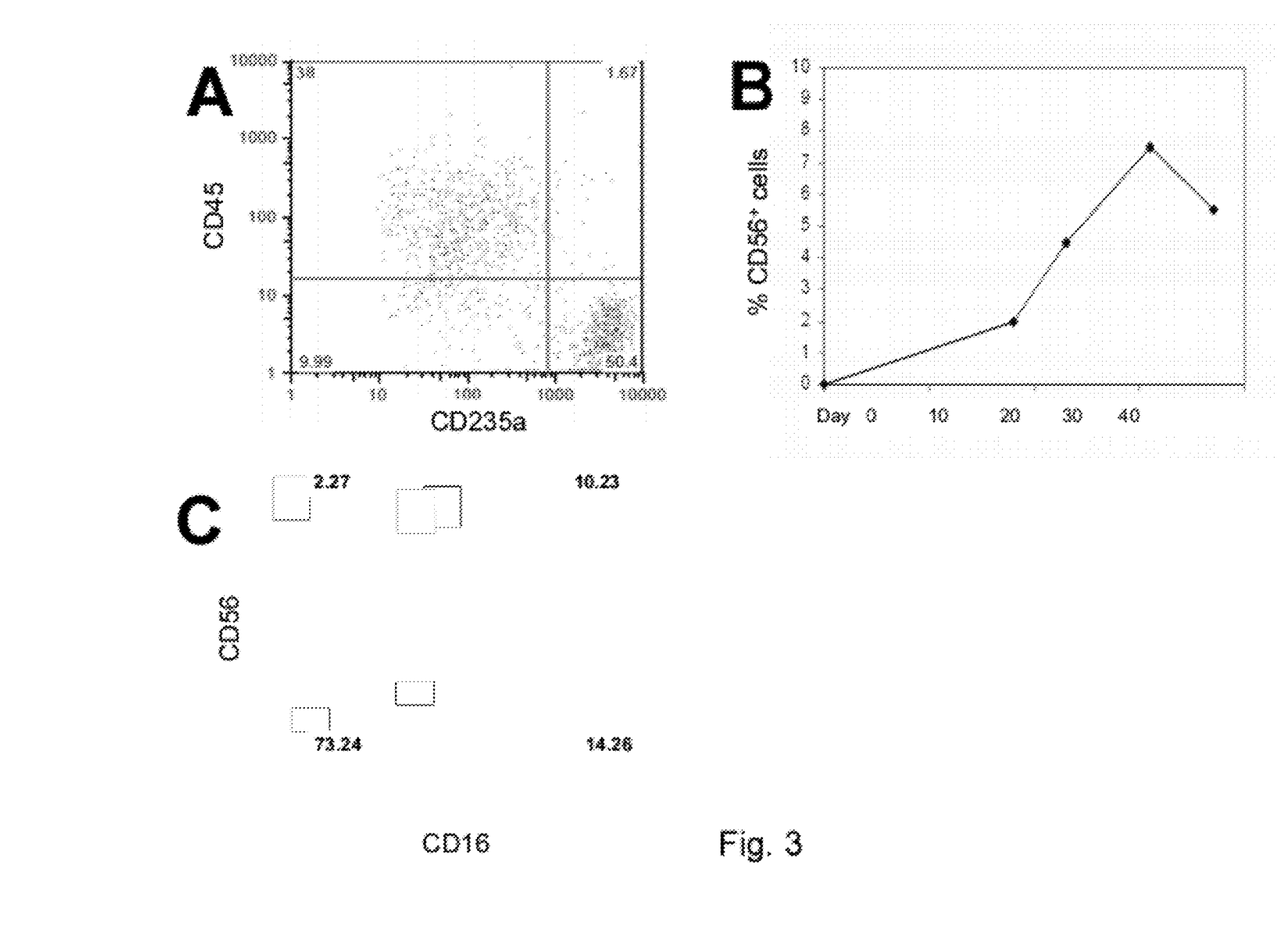
FIG. 3 shows that upon exposure to lymphoid-inducing cytokines, hESC-derived hemangioblasts can give rise to CD56low/CD16+ natural killer cells in a feeder- free culture system in accordance with various embodiments of the present invention. A. During methylcellulose culture, a subset of hemangioblasts acquires the common leukocyte antigen, CD45. B. Transfer of hemangioblasts to liquid culture (containing human serum and a cocktail of cytokines) allows acquisition of NK cell marker, CD56 C. Emergence of CD56low/CD16+ NK cells after total of 28-40 days differentiation.
Figure 4:
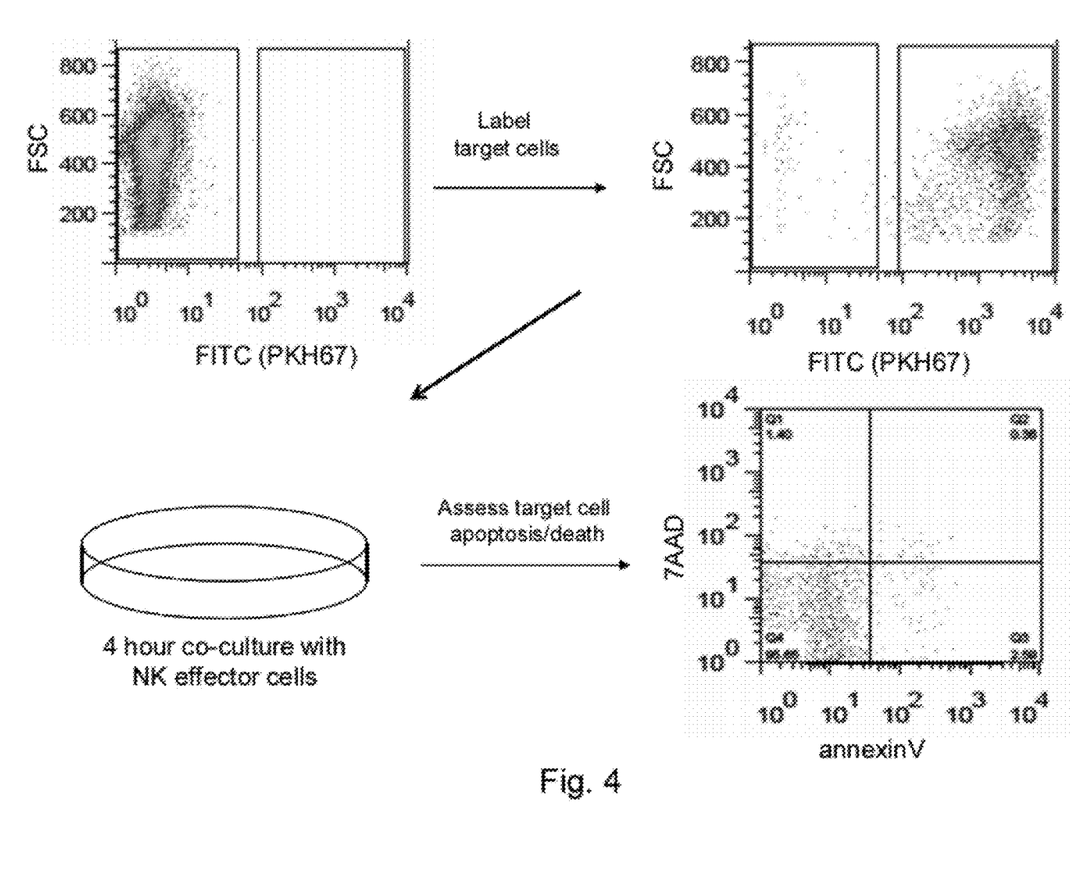
FIG. 4 shows that similar to the classic 51Cr release assay, intracellular flow cytometry can be used to assess NK-mediated cellular cytotoxicity in accordance with various embodiments of the present invention.
Figure 5:
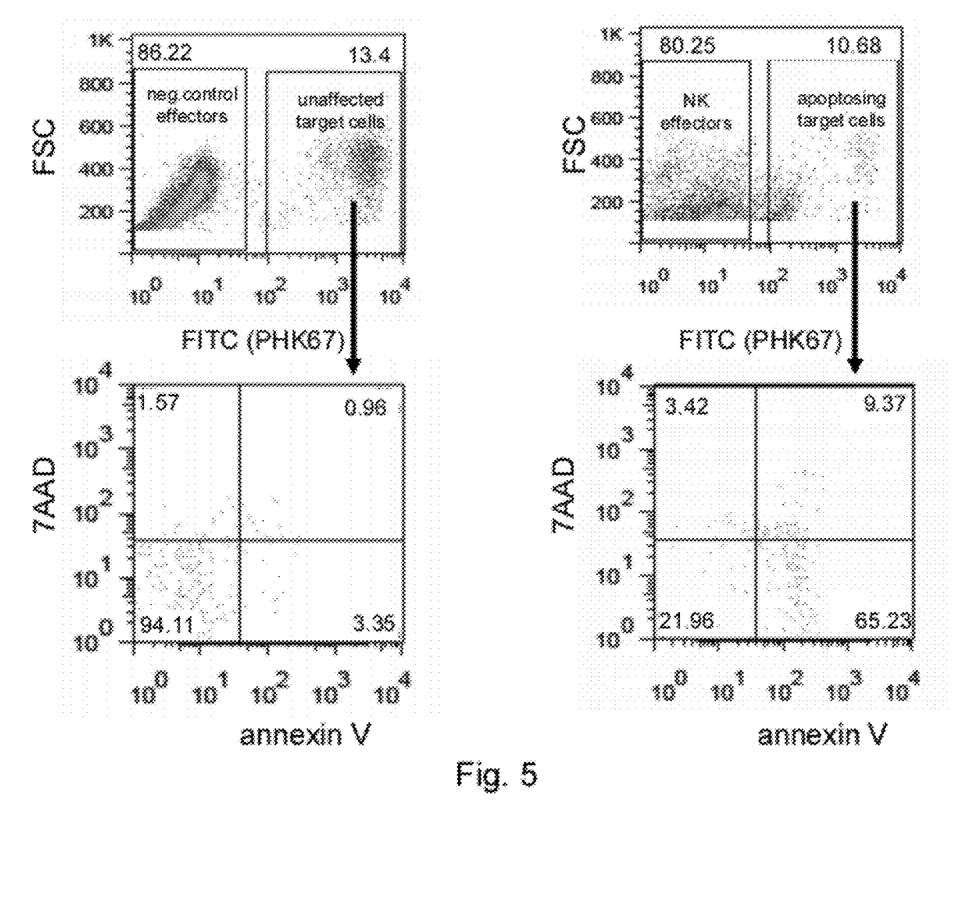
FIG. 5 shows that hemangioblast-derived NK effector cells can induce apoptosis in K562 erythroleukemia target cells after standard 4 hour co-culture in accordance with an embodiment of the present invention.
Figure 6:
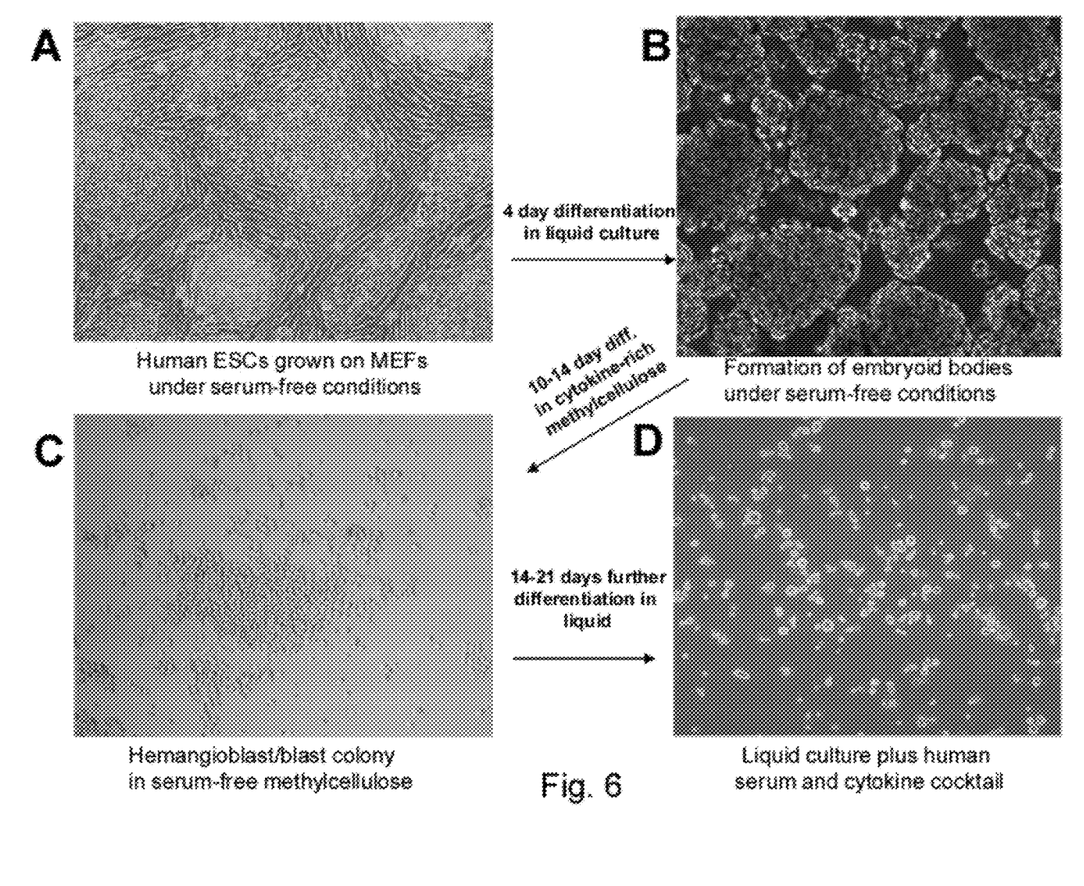
FIG. 6 shows a process of generating the NK cells in accordance with an embodiment of the present invention.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed, J. Wiley & Sons (New York, N.Y. 2001); and Sambrook and Russel, *Molecular Cloning: A Laboratory Manual,* 3$^{rd}$ ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The term "embryonic stem cells" (ES cells) is used-herein-as it is used in the art. This term includes cells derived from the inner cell mass of human blastocysts or morulae, including those that have been serially passaged as cell lines. The ES cells may be derived from fertilization of an egg cell with sperm, as well as using DNA, nuclear transfer, parthenogenesis, or by means to generate ES cells with homozygosity in the HLA region. ES cells are also cells derived from a zygote, blastomeres, or blastocyst-staged mammalian embryo produced by the fusion of a sperm and egg cell, nuclear transfer, parthenogenesis, androgenesis, or the reprogramming of chromatin and subsequent incorporation of the reprogrammed chromatin into a plasma membrane to produce a cell. Embryonic stem cells, regardless of their source or the particular method use to produce them, can be identified based on (i) the ability to differentiate into cells of all three germ layers, (ii) expression of at least Oct-4 and alkaline phosphatase, and (iii) ability to produce teratomas when transplanted into immunodeficient animals.

As used herein, the term "pluripotent stem cells" includes embryonic stem cells, embryo-derived stem cells, and induced pluripotent stem cells, regardless of the method by which the pluripotent stem cells are derived. Pluripotent stem cells are defined functionally as stem cells that are: (a)

capable of inducing teratomas when transplanted in immunodeficient (SCID) mice; (b) capable of differentiating to cell types of all three germ layers (e.g., can differentiate to ectodermal, mesodermal, and endodermal cell types); and (c) express one or more markers of embryonic stem cells (e.g., express Oct 4, alkaline phosphatase, SSEA-3 surface antigen, SSEA-4 surface antigen, nanog, TRA-1-60, TRA-1-81, SOX2, REX1, etc). Exemplary pluripotent stem cells can be generated using, for example, methods known in the art. Exemplary pluripotent stem cells include embryonic stem cells derived from the ICM of blastocyst stage embryos, as well as embryonic stem cells derived from one or more blastomeres of a cleavage stage or morula stage embryo (optionally without destroying the remainder of the embryo). Such embryonic stem cells can be generated from embryonic material produced by fertilization or by asexual means, including somatic cell nuclear transfer (SCNT), parthenogenesis, and androgenesis. Further exemplary pluripotent stem cells include induced pluripotent stem cells (iPS cells) generated by reprogramming a somatic cell by expressing combination of factors (herein referred to as reprogramming factor). iPS can be generated using fetal, postnatal, newborn, juvenile, or adult somatic cells. In certain embodiments, factors that can be used to reprogram somatic cells to pluripotent stem cells include, for example, a combination of Oct4 (sometimes referred to as Oct 3/4), Sox2, c-Myc, and Klf4. In other embodiments, factors that can be used to reprogram somatic cells to pluripotent stem cells include, for example, a combination of Oct 4, Sox2, Nanog, and L in28. In other embodiments, somatic cells are reprogrammed by expressing at least 2 reprogramming factors, at least three reprogramming factors, or four reprogramming factors. Induced pluripotent stem cells can be produced by expressing a combination of reprogramming factors in a somatic cell. In certain embodiments, at least two reprogramming factors are expressed in a somatic cell to successfully reprogram the somatic cell. In other embodiments, at least three reprogramming factors are expressed in a somatic cell to successfully reprogram the somatic cell. In other embodiments, at least four reprogramming factors are expressed in a somatic cell to successfully reprogram the somatic cell. Induced pluripotent stem cells can be produced by protein transduction of reprogramming factors in a somatic cell. In certain embodiments, at least two reprogramming-proteins are transduced into a somatic cell to successfully reprogram the somatic cell. In other embodiments, at least three reprogramming proteins are transduced into a somatic cell to successfully reprogram the somatic cell. In other embodiments, at least four reprogramming proteins are transduced into a somatic cell to successfully reprogram the somatic cell.

In other embodiments, additional reprogramming factors are identified and used alone or in combination with one or more known reprogramming factors to reprogram a somatic cell to a pluripotent stem cell. Induced pluripotent stem cells are defined functionally and include cells that are reprogrammed using any of a variety of methods (integrative vectors, non-integrative vectors, chemical means, etc).

The pluripotent stem cells can be from any species. Embryonic stern cells have been successfully derived in, for example, mice, multiple species of non-human primates, and humans, and embryonic stem-like cells have been generated from numerous additional species. Thus, one of skill in the art can generate embryonic stem cells and embryo-derived stem cells from any species, including but not limited to, human, non-human primates, rodents (mice, rats), ungulates (cows, sheep, etc), dogs (domestic and wild dogs), cats (domestic and wild cats such as lions, tigers, cheetahs), rabbits, hamsters, gerbils, squirrel, guinea pig, goats, elephants, panda (including giant panda), pigs, raccoon, horse, zebra, marine mammals (dolphin, whales, etc.) and the like. In certain embodiments, the species is an endangered species. In certain embodiments, the species is a currently extinct species.

Similarly, iPS cells can be from any species. iPS cells have been successfully generated using mouse and human cells. iPS cells have been successfully generated using embryonic, fetal, newborn, and adult tissue. Accordingly, one can readily generate iPS cells using a donor cell from any species. Thus, one can generate iPS cells from any species, including but not limited to, human, non-human primates, rodents (mice, rats), ungulates (cows, sheep, etc), dogs (domestic and wild dogs), cats (domestic and wild cats such as lions, tigers, cheetahs), rabbits, hamsters, goats, elephants, panda (including giant panda), pigs, raccoon, horse, zebra, marine mammals (dolphin, whales, etc.) and the like. In certain embodiments, the species is an endangered species. In certain embodiments, the species is a currently extinct species.

Induced pluripotent stem cells can be generated using, as a starting point, virtually any somatic cell of any developmental stage. For example, the cell can be from an embryo, fetus, neonate, juvenile, or adult donor. Exemplary somatic cells that can be used include fibroblasts, such as dermal fibroblasts obtained by a skin sample or biopsy, synoviocytes from synovial tissue, foreskin cells, cheek cells, or lung fibroblasts. Although skin and cheek provide a readily available and easily attainable source of appropriate cells, virtually any cell can be used. In certain embodiments, the somatic cell is not a fibroblast.

The terms "hemangioblast" and "hemangio-colony forming cell" will be used interchangeably throughout this application. The cells have numerous structural and functional characteristics. Amongst the characteristics of these cells is the ability to engraft into the bone marrow when administered to a host. These cells can be described based on numerous structural and functional properties including, but not limited to, expression (RNA or protein) or lack of expression (RNA or protein) of one or more markers. Hemangio-colony forming cells are capable of differentiating to give rise to at least hematopoietic cell types or endothelial cell types. Hemangio-colony forming cells are preferably bi-potential and capable of differentiating to give rise to at least hematopoietic cell types and endothelial cell types. As such, hemangio-colony forming cells of the present invention are at least uni-potential, and preferably bi-potential. Additionally however, hemangio-colony forming cells may have a greater degree of developmental potential and can, in certain embodiments, differentiate to give rise to cell types of other lineages. In certain embodiments the hemangio-colony forming cells are capable of differentiating to give rise to other mesodermal derivatives such as cardiac cells (for example, cardiomyocytes) and/or smooth muscle cells.

The terms "non-engrafting hemangioblasts" or "non-engrafting hemangio cells" are used throughout this application to refer to a population of cells that share some of the characteristics of hemangio-colony forming cells. However, the non-engrafting hemangio cells are distinguishable in that they do not engraft into the bone marrow when administered to an immunodeficient host. Despite this difference, non-engrafting hemangio cells may share one or more than one (2, 3, 4, 5, 6, 7, 8, 9, 10) of the functional or structural characteristics and properties of hemangio-colony forming cells. For example, in certain embodiments, the non-engrafting hemangio cells are loosely adherent to each other. In other embodiments, the non-engrafting hemangio cells do not express one or more than one (2, 3, 4) of the following proteins: CD34, KDR, CD133, CD31. Without being bound by theory, non-engrafting hemangio cells may provide a distinct stem cell population that is somewhat more committed than hemangio-colony forming cells, and yet still capable of producing a range of hematopoietic cell types.

The inventors have developed an in vitro culture system to produce cells with immunotherapeutic potential from human ESCs. This strategy differs from prior art in that it involves the use of hESC-derived hemangioblasts as an intermediate cell source. The inventors have been able to direct the differentiation of hemangioblasts into both natural killer (NK) and dendritic cells (DCs) using feeder-free culture conditions. NK cells, which arise through the lymphoid lineage and are part of the innate immune system, may be used in anti-cancer therapy as they have been found to detect and kill certain types of tumor cells. DCs, which mostly arise through the myeloid lineage (from monocytes) and are part of the adaptive immune system, may be used to enhance antigen-specific immune responses through their ability to present antigen to and stimulate both naïve and memory T cells (e.g. DC-based vaccine therapy).

Interplay between various activating and inhibitory signals control the three main functions of NK cells, which are cytokine release, natural cytotoxicity, and antibody-dependent cellular cytotoxicity. Using hemangioblasts generated from both H7 and HuES-3 hESC lines, the inventors have been able to produce mature CD56low/−, CD16+ NK cells and found that their production does not require the use of stromal feeder layers. The differentiation procedure involves an initial 4 day culture to generate embryoid bodies, followed by a 10-14 day culture in methylcellulose supplemented with a set of cytokines and growth factors for the production and expansion of a hemangioblastic population. An additional 14-21 days in liquid culture plus human serum and a cocktail of cytokines allows for the differentiation of NK cells as assessed by flow cytometry. A non-radioactive cytotoxicity assay similar to the 51Cr release assay shows that these hemangioblast-derived NK cells harbor natural cytotoxicity function as they are able to effectively induce apoptosis in target K562 erythroblastic leukemia cells after a standard 4 hr co-culture. Using hemangioblasts as an intermediary cell source may enhance the capability and/or efficiency of hESCs to differentiate in vitro and importantly, allow for the development of feeder-free systems for the production of cells with immunotherapeutic potential.

Embodiments of the present invention provide a method of generating lymphoid lineage cells. In various embodiments, the present invention provides a method of generating natural killer (NK) cells.

In various embodiments, the method of generating NK cells comprise& providing hemangioblasts; plating and culturing the hemangioblasts on methylcellulose and IL2, IL3, IL6, IL7, IL15, SCF and FL; harvesting the cells; and replating/culturing the harvested cells in liquid media comprising human serum, IL7, IL15, SCF and FL.

In various embodiments, the liquid media is changed weekly. In various embodiments, the methylcellulose is H4236 methylcellulose. In other embodiments, the methylcellulose is H4536 methylcellulose. In various embodiments, the concentrations of the cytokines are IL2 (5-10 ng/ml), IL3 (1-10 ng/ml), IL6 (1-10 ng/ml), IL7 (5-20 ng/ml), IL15 (5-10 ng/ml), SCF (10-50 n/ml), and FL (10-50 ng/ml). In various embodiments, harvesting the cells is done after 6-8 days of culturing the cells. In various embodiments, the cells are cultured for an additional 14-21 days after the cells are replated. In various embodiments, the liquid media is αMEM or DMEM:F12.

In another embodiment, the method of generating natural killer (NK) cells comprises: providing hemangioblasts; culturing the hemangioblasts in liquid media comprising IL2, IL3, IL6, IL7, IL15, SCF, and human serum; harvesting the cells; and culturing the harvested cells in liquid media comprising human serum, IL7, IL15, SCF and FL.

In various embodiments, the liquid media is changed weekly. Similar to the foregoing, in various embodiments the concentrations of the cytokines are IL2 (5-10 ng/ml), IL3 (1-10 ng/ml), IL6 (1-10 ng/ml), IL7 (5-20 ng/ml), IL15 (5-10 ng/ml); SCF (10-50 ng/ml), and FL (10-50 ng/ml). In various embodiments, harvesting the cells is done after 6-8 days of culturing the cells. In various embodiments, the cells are cultured for an additional 14-21 days after the cells are replated. In various embodiments, the liquid media is αMEM or DMEM:F12.

Various embodiments of the present invention provide for natural killer cells generated by the methods of the present invention. In various embodiments, the NK cells are provided in a pharmaceutically acceptable composition comprising a quantity of the NK cells generated by the methods of the present invention.

Other embodiments of the present invention provide for a method to generate dendritic cells (DCs). In one embodiment, the method to generate DCs comprises: providing hemangioblasts; plating and culturing the hemangioblasts in liquid media comprising human serum, SCF, FL, IL3 and GM-CSF; adding IL4 to the liquid media; and further culturing the cells.

In other embodiments, the method further comprises adding a cytokine cocktail comprising IL1b, TNFα and IL6 to induce maturation of the DCs. In further embodiments, the cytokine cocktail further comprises a cytokine selected from the group consisting of PGE2, IFNα2b, poly I:C, IFNγ and combinations thereof. In other embodiments, the method further comprising adding LPS, IFNγ and/or S-28463 to stimulate IL12p70 production from the DCs and/or HLA-DR expression from the DCs.

In various embodiments, the liquid media is changed every 6 to 7 days. In various embodiments the liquid media is αMEM or DMEM:F12. In various embodiments, the cells are cultured for 7-11 days. In various embodiments, the IL4 is, added after the cells are cultured for 7-11 days. In various embodiments, the cells are cultured for an additional 8-10 days after adding the IL4.

In various embodiments, the concentrations of the human serum, SCF, FL, IL3 and GM-CSF are human serum (10-20%), SCF (20-100 ng/ml), FL (10-50 ng/ml), IL3 (5-50 ng/ml) and GM-CSF (50-100 ng/ml). In another embodiment, the concentration of IL4 is 50-100 ng/ml. In various embodiments, the concentrations of IL1b, TNFα and IL6 are IL1b (10 ng/ml), TNFα (10 ng/ml) and IL6 (150 ng/ml). In various embodiments, the concentrations of PGE2, IFNα2b, poly I:C, and IFNγ are PGE2 (1 µg/ml), IFNα2b (3000 units/ml), poly I:C (20 µ/ml), and IFNγ (20 ng/ml).

Since the efficiency of producing dendritic cells from hemangioblasts is relatively good, future work with DCs can involve optimizing conditions for and developing various new functional assays. For example, altering the components that comprise the DC maturation cocktail may improve the IL12p70 secretion assay. While the inventors currently use a cocktail of 6 different cytokines for maturation, the addition of LPS and/or IFNγ may be required in order to stimulate IL12p70 production from blast-derived DCs. Similarly, the synthetic compound, S-28463 may help increase-both IL12p70 production and HLA-DR expression.

Various embodiments of the present invention provide for dendritic cells generated by the methods of the present invention. In various embodiments, the DCs are provided in a pharmaceutically acceptable composition comprising a quantity of the DCs generated by the methods of the present invention.

In various embodiments of the present invention, the hemangioblast may be obtained by a method comprising: providing hESCs; culturing the hESCs in media comprising cytokines to generate embryoid bodies (EBs); disaggregating the EBs; filtering individual cells; seeding the individual cells into methylcellulose comprising TPO, VEGF, FL, and bFGF; and harvesting the blast-like cells from methylcellulose.

In various embodiments the hESCs are first cultured for 4 days before disaggregating the EBs. In various embodiments, the cytokines to generate embryoid bodies comprise VEGF and BMP4. In various embodiments, VEGF and BMP4 are used throughout the EB formation. In another embodiment, the cytokines to generate embryoid bodies further comprise bFGF. In one embodiment, the bFGF is added after the first 2 days of culturing the hESCs. In various embodiments, disaggregation of the EBs comprises, disaggregating the EBs with trypsin and then inactivating the trypsin with serum-containing media. In one embodiment, the trypsin is 0.05%. In various embodiments, filtering the individual cells comprise filtering the individual cells through a 40 µM cell strainer. In various embodiments, the metheylcellulose is H4436 or H4536 methylcellulose. In various embodiments the concentration of cytokines are TPO (50 µg/ml), VEGF (50 µg/ml), FL (50 µg/ml), and bFGF (20-50 µg/ml). In various embodiments, the blast-like cells are harvested from methylcellulose between day 6 and day 10.

In particular embodiments, such as preparing hemangioblasts for use in generating NK cells, the methylcellulose may comprise additional cytokines. These additional cytokines are selected from the group consisting of IL2, IL7, IL15 and combinations thereof. In various embodiments, the concentrations of these cytokines are IL2 (1-10 µg/ml), IL7 (1-20 µg/ml), and IL15 (1-10 µg/ml). In various embodiments, methylcellulose cultures are plated at a concentration of 50,000 to 150,000 cells/ml.

In a particular embodiment, the hemangioblasts are generated in an erythropoietin free methylcellulose. In one embodiment the erythropoietin free methylcellulose is H4536 methylcellulose.

In alternate embodiments, pluripotent stem cells (including iPS cells and human iPS cells) are used in place of hESCs. In other embodiments, the hemangioblasts may be non-engrafting hemangioblasts.

International Application Nos. PCT/US09/43050 and PCT/US09/43043 both filed May 6, 2009 and herein incorporated by reference as though fully set forth in their entirety, provide additional guidance on the generation of hemangioblasts and non-engrafting hemangioblasts.

In various embodiments, the present invention provides pharmaceutical compositions including a pharmaceutically acceptable excipient along with a therapeutically effective amount of the natural kill cells or dendritic cells of the present invention. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral.

"Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Initial Differentiation

The initial differentiation procedure for both cell types is the same and involves, a 4 day culture of hESCs in Stemline II (Sigma) plus cytokines in order to generate embryoid bodies (EBs). The cytokines, VEGF and BMP4 are used throughout the EB culture while bFGF is added after the first 2 days. After 4 days total, the resulting EBs are disaggregated with 0.05% trypsin and then the trypsin is inactivated with serum-containing media. Individual cells are subsequently filtered through a 40 µM cell strainer, counted, and seeded into H4436 or H4536 methylcellulose (Stem Cell Technologies) containing additional cytokines, such as TPO (50 µg/ml), VEGF(50 µg/ml), FL (50 µg/ml) and bFGF (20-50 µg/ml). For NK differentiation, the cytokines IL2 (1-10 µg/ml), IL7 (1-20 µg/ml), and/or IL15 (1-10 µg/ml) may also be added at this stage. Methylcellulose cultures are plated at a concentration of 50,000 to 150,000 cells per ml for the production and expansion of a hemangioblastic population. Blast-like cells are harvested from methylcellulose between day 6 and 10 and further differentiated by one of the following procedures.

Example 2

NK Differentiation

Blast cells may be replated in H4236 methylcellulose plus IL2 (5-10 ng/ml), IL3 (1-10 ng/ml), IL6 (1-10 ng/ml), IL7 (5-20 ng/ml), ILL5 (5-10 ng/ml), SCF (10-50 ng/ml), and FL (10-50 ng/ml) or in liquid culture containing the same cytokines and 10-20% human serum. After 6-8 days culture, cells are harvested and replated in liquid media (αMEM or DMEM:F12) plus 10-20% human serum and the cytokines IL7 (5-20 ng/ml), IL15 (5-10 ng/ml), SCF (10-50 ng/ml), and FL (10-50 ng/ml) for an additional 14-21 days. Weekly media changes are used to refresh the cytokine cocktail.

Flow cytometry is used intermittently throughout the differentiation procedure to assess the immunophenotype of cells and the acquisition of NK cell surface markers. Cell surface markers include CD34, CD45, CD56, CD16, CD94, NKG2D, CD3, CD7, CD4, CD8a, and CD45RA. Tests to examine the function of hemangioblast-derived NK cells include. (1) natural cytotoxicity assay using K562 erythroleukemia target cells, (2) IFNγ production in response to IL12/IL18 or phorbol myristate acetate treatment, (3) intracellular flow cytometry for presence of perforin and granzyme B enzymes, and (4) antibody-dependent cellular cytotoxicty assay using Raji cells and anti-CD20 antibodies.

Thus far, the inventors have been able to generate NK cells from both H7 and HuES3 hESCs. A non-radioactive cytotoxicity assay similar to the $^{51}$Cr release assay shows that our hemangioblast-derived NK cells harbor natural cytoxicity function as they are able to effectively include apoptosis in target K562 erythroblastic leukemia cells after a standard 4 hr co-culture.

Example 3

DC Differentiation

Blast cells are plated in liquid media (αMEM or DMEM: F12) plus 10-20% human serum and the cytokines, SCF (20-100 ng/ml), FL (10-50 ng/ml), IL3 (5-50 ng/ml), and GM-CSF (50-100 ng/ml). After 7-11 days culture, IL4 (50-100 ng/ml) is also added to the culture and cells are allowed to grow for in additional 8-10 days. Media changes are performed every 6-7 days. An additional cytokine cocktail (10 ng/ml IL1b, 10 ng/ml TNFγ, 150 ng/ml IL6) can be added to the culture for 48 hours in order to induce maturation of DCs.

Flow cytometry is used intermittently throughout the differentiation procedure to assess the immunophenotype of cells and the acquisition of DC surface markers. Cell surface markers include CD11c, CD209 (DC-SIGN), HLA ABC (MHC class I), HLA DR (MHC class II), CD1a, and CD14. Maturation is assessed by the acquisition of T-cell co-stimulatory receptor, CD83 while the expression of CD209, HLA DR, and CD11c may also increase upon maturation. Additional cytokines such as 1 µg/ml PGE2, 3000 units/ml IFNα2b, 20 µg/ml poly I:C, or IFNγ 20 ng/ml may be added to the maturation cocktail to enhance DC functional response in certain assays. Assays to address the functionality of hemangioblast-derived DCs include (1) antigen uptake via ovalbumin (BD Biosciences) processing, (2) transwell migration in response to -the chemoattractant, MIP-3b, (3) allogenic mixed lymphocyte reaction assay to determine the ability of DCs to increase proliferation of HLA-mismatched T cells; (4) IL12-p70 secretion upon DC stimulation, and (5) antigen presenting assay to determine if antigen-loaded DCs can induce IFNγ production in previously antigen-primed peripheral blood mononuclear cells.

The inventors have been able to generate DCs from both HuES3 and MA01 hESCs. Upregulation of CD83, HLA-DR, CD11c, and CD209 in response to the 48 hour maturation cytokine cocktail was observed. These DCs are found to be able to uptake and proteolyse DQ-ovalbumin in a 30 minute assay.

Example 4

Alteration of Hemangioblast Growth Conditions

The above NK and DC differentiation procedures were performed using hemangioblasts grown in 114436 methylcellulose. However, 114536, an erythropoietin-free methylcellulose from Stem Cell Technologies can also be used to efficiently generate hemangioblasts. These "epo minus" hemangioblasts are quite similar to the original "epo plus" blasts; they are capable of differentiating into a variety of hematopoietic and vascular cell types. Preliminary results suggest that the use of H4536 may provide a significant advantage over H4436 methylcellulose for the differentiation of hemangioblasts into various hematopoietic lineages, including NK cells and DCs. The absence of epo in the blast growth media has been found to reduce the percentage of cells expressing the erythrocyte marker CD235a and increase the percentage of cells expressing CD34, CD45, and CD41a. Due to this difference in cell surface marker expression, "epo-minus" growth conditions may enhance differentiation down myeloid and/or lymphoid lineages.

Example 5

Generation of MKs from iPS Cells

Using OP9 co-culture system, the inventors show that MKs can be generated from iPS cells. A few thousand CD41a+ MKs were generated from a few hundred thousand iPS cells.

Example 6

NK Cell Differentiation from Human ESCs

Differentiation procedure was performed as follows:

H7 ESCs were differentiated into embryoid bodies (EBs) for 4 days. EBs were harvested and transferred to cytokine-rich methylcellulose for 10-15 days for hemangioblast production and expansion. Hemangioblasts were harvested and placed into feeder-free liquid culture medium plus 10-20% human AB serum, with a panel of cytokines for an additional 14-17 days with media half changes every 3-4 days.

Immunophenotyping (Using Flow Cytometry):

Immature NK cells were CD56bright, CD16lo, KIRlo, CD117+, CD94−, NKG2D+. By using a variation of the above procedure, 20-30% of the viable cells after 32 days of differentiation were CD56+ CD16−. Mature NK cells were CD56dim, CD16hi, KTRhi, CD117lo/−, CD94+, NKG2D+. By using the above procedure, 20% of the viable cells after 31 days of differentiation were CD56-CD16+ and 5% of them were CD56loCD16+.

Functional Assays:

Natural cytotoxicity: mature NK cells can elicit apoptosis of target cells such as human K562 erythroleukemia, MCF7, U87, PC3, NTERA2 cells. A "3FC" assay is used to assess efficiency of cytotoxicity. It is similar to 51Cr release assay but does not require radioactivity. See Derby et al., Immunol. Letters 78: 35-39 (2001). The heterogeneous population of mature NK cells described above (item B2-a) was found to elicit apoptosis in 65-70% of K562 cells in a standard 4 hour experiment.

Antibody-dependent cell-mediated cytotoxicity (ADCC): The FcγRIII (CD16) on the NK cell surface binds to the fc region of anti-CD20 antibodies attached to target cells and induces ADCC. Raji cells (derived from Burkett's lymphoma) are preincubated with anti-CD20 antibody and used as targets in ADCC assay. (Tsirigotis et al, J of Steroid Biochem and Mol Bio 108: 267-271 (2008)).

IFNγ cytokine production: Immature NK cells produce large amounts of IFNγ in response to overnight treatment with PMA (phorbol myristate acetate) plus ionomycin or IL12 plus IL18. IFNγ secretion is blocked with brefeldin a, cells are stained for cell surface markers and IFNγ using intracellular flow cytometry. See Woll et al. J. of Immunol. 175: 5095-5103 (2005).

In vivo immunotherapy potential of NK cells using xenograft mouse model: Bioluminescent (luciferase-containing) K562 cells are injected into NOD/SCID mice for engraftment of tumors, followed by bolus of NK cells and daily IP injections of IL2 and IL15. Bioluminescence imaging is used to monitor in vivo NK immunotherapeutic potential over time. See: Woll et al. Blood 113 (24): 6094-6101 (2009).

Example 7

By using hemangioblasts as bone-marrow-repopulating cells or by differentiating them into dendritic, natural killer, T cells, and/or mesenchymal stem cells (MSCs), we can produce large-scale, effective cell-based therapies to combat cancer, HIV, and/or automimmune diseases. The inventors were able to achieve differentiation of dendritic cells (DCs) from both hESCs and iPS cells with 40-55% efficiency. A side by side comparison to DCs derived from human bone marrow, in addition to two new functional assays, has now confirmed that the hESC-derived DCs share many comparable features with human BM-derived DCs and also identified areas that need further optimization. For natural killer cell differentiation, a side by side comparison to human bone marrow-derived NK cells has confirmed that in vitro NK cell differentiation is not very efficient, even when using a bone marrow cell source. The inventors have found that blast-derived NK cells display natural cytotoxicity capabilities. Antibody-dependent cellular cytotoxicity assays are performed. For T cell differentiation, the inventors have successfully created a human delta-ligand expressing OP9 stroma cell line to stimulate Notch signaling and are using this stroma cell line to stimulate T cell differentiation of hemangioblasts.

Hemangioblast-derived dendritic cells (40-55% efficiency)

Cell surface markers: CD11c, 45, 209 show comparable expression on blastderived DCs and human bone marrow-derived DCs, while HLA-DR is expressed at much lower levels on blast DCs than on human BM DCs.

Functional assays (previously reported on antigen uptake and migration assays). IL12-p70 secretion: IL12p70 is secreted by mature DCs in order to elicit a Th1-directed response from CD4+ T cells. Human BM-derived DCs can produce >500 pg/ml of IL12p70 yet blast-derived DCs did not produce any detectable IL12p70 upon maturation. Mixed lymphocyte reaction (MLR) assay: The MLR assay determines the ability of DCs to stimulate proliferation of allogenic T cells. Cord blood mononuclear cells (CBMCs, which include T cells) were used as responders, fluorescently labeled, and their proliferation was measured after 4-5 days coculture with immature or mature blast-derived DCs. Preliminary results show that the responder cells proliferate in response to mature (m)DCs.

Hemangioblast-derived natural killer cells: Cell surface markers. CD45; CD7, CD94, CD56, CD16, and NKG2D were evaluated in blast-derived and human bone marrow-derived NK cells.

NK differentiation efficiency: Recombinant human Sox7 protein was being investigated for its ability to increase the pool of CD34+ starting progenitors for NK differentiation. Results suggest that rhSox7 does not dramatically affect % of CD34+ cells. Murine AFT024 was investigated as a stroma feeder layer that may provide critical cell-cell contacts and secreted factors for NK cell differentiation. As indicated by cell surface marker expression, AFT024 stroma co-culture did not enhance NK differentiation of either human BM or blasts.

Hemangioblast-derived T cells: Notch signaling is crucial for T cell differentiation. As such, the cDNA for human delta-like ligand 1 (hDLL1) was cloned into an MSCV-ireS-GFP based retroviral vector and used the resulting viral supernatant to infect OP9 stroma cells. Upon viral integration, OP9 cells will express hDLL1 on their cell surface and be gfp positive. FACS-based sorting was used to purify the highest gfp-positive cells from the heterogeneous pool of infected OP9 cells. These OP9-hDL1S ("S" for sorted) were expanded and characterized. Q-RT-PCR, immunofluorescence, and flow cytometry all confirm expression of the hDLL1 protein in these cells.

Example 8

Both cord blood and peripheral blood mononuclear cells are used as responders and the inventors use human bone marrow-derived DCs as positive control effectors.

E4BP4 has been shown to be critical for NK lineage development (see Gascoyne et al. Nature Immunology 10(10): 1118-1125, 2009) and may provide the transcriptional program necessary for more efficient in vitro.

NK cell differentiation. The inventors clone E4BP4 cDNA into a retroviral vector for its overexpression in hemangio-blasts and evaluate its ability to increase NK differentiation. RT-PCR is used to monitor the expression of various KIR receptor isoforms and the enzymes, perforin and granzyme B, which are critical for NK cell functionality. For functional assays, the inventors have shown that blast-derived NK cells display natural cytotoxicity, so their antibody-dependent cellular cytotoxicty (ADCC) capabilities are assessed. Required reagents for the ADCC assay include the Burkitt's lymphoma-derived Raji cells and anti-CD20 antibodies. Co-culture of CD20-marked Raji cells with NK cells should elicit a specific. ADCC response, which will be monitored through flow cytometric means.

NK REFERENCES

1. Woll, P, et al. J. of Immunology. 175: 5095-5103 (2005).
2. Woll, P et al. Blood 113(24):6094-101 (2009).
3. Bordoni et al. Hepatology 39: 1508-1516 (2004).
4. Tabatoabaei-Zavareh et al. PLOS One Issue 2, e232 (2007).
5. McCullar, V et al. Exp. Hematology 36(5): 598-608 (2008).
6. Freud, A G et al. Immunity. 22:295-304 (2(05).
7. Yu, H et al. Blood 92 (10): 3647-3657 (1998).

DC REFERENCES

1. Su et al. Clinical Cancer Research 14(19): 6207-6217 (2008).
2. Tseng et al. Regenerative Medicine 4(4): 513-526 (2009).
3. Bandi et al. AIDS Research and Therapy 5:1 (2(08). (open-access)
4. Slukvin, II et al. J of Immunology 176: 2924-2932 (2006).

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the worth and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, if will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method to generate dendritic cells (DCs), comprising:
   providing hemangioblasts;
   culturing the hemangioblasts in liquid media comprising human serum, SCF, FL, IL3 and GM-CSF;
   adding IL4 to the liquid media; and
   further culturing the hemangioblasts to generate the DCs.

2. The method of claim 1, wherein culturing the hemangioblasts is for about 7 to 11 days.

3. The method of claim 1, wherein further culturing of the hemangioblast after the addition of IL4 is for about 8 to 10 days.

4. The method of claim 1, further comprising adding a cytokine mixture comprising IL1b, TNFα and IL6 to induce maturation of the DCs.

5. The method of claim 4, wherein the cytokine mixture is added for about 48 hours.

6. The method of claim 4, wherein the cytokine mixture further comprises a cytokine selected from the group consisting of PGE2, IFNα2b, poly I:C, IFNγ and combinations thereof.

7. The method of claim 1, further comprising adding LPS, IFNγ and/or S-28463 to stimulate IL12p70 production from the DCs and/or HLA-DR expression from the DCs.

8. The method of claim 1, wherein the concentration of SCF is about 20-100 ng/ml, FL is about 10-50 ng/ml, IL3 is about 5-50 ng/ml, GM-CSF is about 50-100 ng/ml, and IL4 is about 50-100 ng/ml.

9. The method of claim 4, wherein the concentration of IL1b is about 10 ng/ml, TNFγ is about 10 ng/ml, and IL6 is about 150 ng/ml.

10. The method of claim 6, wherein the concentration of PGE2 is about 1 μg/ml, IFNα2b is about 3000 units/ml, poly I:C is about 20 μg/ml, and IFNγ is about 20 ng/ml.

11. The method of claim 1, wherein the DCs are mature DCs and express CD83.

12. The method of claim 1, wherein the DCs are mature DCs and the expression of CD209, HLA DR and/or CD11c is increased.

* * * * *